United States Patent [19]
Kennedy

[11] Patent Number: 5,397,985
[45] Date of Patent: Mar. 14, 1995

[54] METHOD FOR THE IMAGING OF CASING MORPHOLOGY BY TWICE INTEGRATING MAGNETIC FLUX DENSITY SIGNALS

[75] Inventor: W. David Kennedy, Carrollton, Tex.

[73] Assignee: Mobil Oil Corporation, Farifax, Va.

[21] Appl. No.: 15,012

[22] Filed: Feb. 9, 1993

[51] Int. Cl.⁶ .................. G01N 27/82; G01B 7/10; G01D 5/12; G01R 13/00
[52] U.S. Cl. .................. 324/221; 324/226; 324/229; 346/33 P; 348/32; 348/84; 348/162
[58] Field of Search ............... 324/219, 220, 221, 226, 324/346, 229-231; 346/33 P, 33 F, 33 M; 348/84, 85, 162, 32

[56] References Cited

U.S. PATENT DOCUMENTS

| | | | |
|---|---|---|---|
| 2,684,464 | 7/1954 | Hastings et al. | 324/220 |
| 2,896,155 | 1/1959 | Cook | 324/34 |
| 3,238,448 | 3/1966 | Wood et al. | 324/220 |
| 3,273,054 | 9/1966 | Cook | 324/37 |
| 3,597,678 | 8/1971 | Fearon | 324/37 |
| 3,727,126 | 4/1973 | Kiselman et al. | 324/221 |
| 4,292,589 | 9/1981 | Bonner | 324/221 |
| 4,468,619 | 8/1984 | Reeves | 324/220 |
| 4,591,785 | 5/1986 | Hoehn, Jr. | 324/239 |
| 4,625,165 | 11/1986 | Rothstein | 324/220 |
| 4,751,460 | 6/1988 | Mato, Jr. | 324/221 |
| 4,843,317 | 6/1989 | Dew | 324/221 |
| 4,855,677 | 8/1989 | Clark, Jr. et al. | 324/220 X |

*Primary Examiner*—Gerard R. Strecker
*Attorney, Agent, or Firm*—Alexander J. McKillop; George W. Hager, Jr.

[57] ABSTRACT

Apparatus for 360° azimuthal imaging of steel casing employs a transducer that is rotated around the inside wall of the casing for inducing and measuring variations in induced flux density within the casing as an indication of changes in casing thickness.

3 Claims, 3 Drawing Sheets

METHOD FOR THE IMAGING OF CASING MORPHOLOGY BY TWICE INTEGRATING MAGNETIC FLUX DENSITY SIGNALS

BACKGROUND OF THE INVENTION

Wells drilled for hydrocarbon production are completed with steel casing whose purpose is to control pressure and direct the flow of fluids from the reservoir to the surface. Mechanical integrity of the casing string is important for safety and environmental reasons. The mechanical integrity of a casing string may degrade during the production process due to corrosion which may be induced either mechanically, chemically, or by other means. Regardless of how the corrosion is initiated, or the mechanism by which it progresses, chemical or otherwise, the process removes competent structural material from the casing leaving what remains behind correspondingly thinner and weaker. The state of the mechanical integrity must be estimated or otherwise ascertained by production engineers in order to assess the need for casing repair or replacement prior to catastrophic failure. Several devices for the remote sensing of the casing condition are available. For example, there are casing imaging systems based on acoustical principles. In order to use such systems, casing must be filled with a liquid of constant density whose flow rate is low enough so that the acoustic signals are not lost in noise produced by moving fluids. When conditions favorable for acoustic imaging are not met, mechanical calipers employing numerous tines (50 or 64 have been used) to map casing inner diameter on closely spaced parallel tracks in the casing are used. The mechanical caliper has been suspected of inducing corrosion in some environments.

Various magnetic and electromagnetic techniques have been utilized to detect anomalies in casing, for example, U.S. Pat. Nos. 3,597,678; 4,468,619; and 4,591,785. However, such techniques either have no azimuthal resolution, characterizing the entire casing in terms of a single apparent thickness, or are similar to mechanical calipers in that the azimuthal sampling is limited to a fixed number of sensors. Devices of the latter type are frequently claimed to have 360 degree resolution; however, the actual angular resolution is coarse, being given by the number of sensors on the circumference of the device divided into 360 degrees. For example, twelve such sensors provide an azimuthal resolution of 30°. These devices are not sensitive to the presence of small, localized defects which in time may corrode through the casing, nor can they localize the detected defects to a casing region more precise than a 30° segment of the casing circumference.

SUMMARY OF THE INVENTION

The present invention is directed to a method and system for the 360° azimuthal imaging of steel casing in which a magnetic or electromagnetic transducer is utilized to induce a magnetic flux in the casing and to measure variations in flux density caused by variations in casing thickness.

More particularly, a transducer is positioned inside the casing and in close proximity to the inside wall of the casing. The transducer is maintained at a constant distance from the casing axis during its rotation cycle. This constant distance is maintained regardless of variations in the inside diameter of the casing. The transducer induces a magnetic flux in the portion of the casing adjacent to the transducer. The transducer is rotated about the axis of the casing and continuously measures variations in the flux density within the casing during rotation to produce a true 360° azimuthal flux density response. The transducer is continuously repositioned vertically at a rate determined by the angular velocity of the rotating transducer and the desired vertical resolution of the final image. The transducer thus moves in a helical track near the inner wall of the casing. The measured variations in flux density for each 360° azimuthal scan are continuously recorded as a function of position along the casing to produce a 360° azimuthal sampling of the flux induced in the casing along the selected length.

The measured variations in flux density recorded as a function of position are used to generate an image. For the example of a magnetic transducer, the twice integrated response is correlatable to the casing profile passing beneath the transducer; this response can be calibrated in terms of the distance from the transducer to the casing surface, thus yielding a quantitatively interpretable image of the inner casing surface. In the case of electromagnetic transducers, operating frequencies can be chosen such that the observed flux density is related either to the proximity of the inner casing surface, or alternatively, to the casing thickness. Hence the use of electromagnetic transducers permits the simultaneous detection of both the casing thickness and the proximity of the inner surface; these can be used together to image casing defects both inside and outside the casing, as well as to produce a continuous image of casing thickness.

DESCRIPTION OF THE PREFERRED EMBODIMENT

Figure 1:
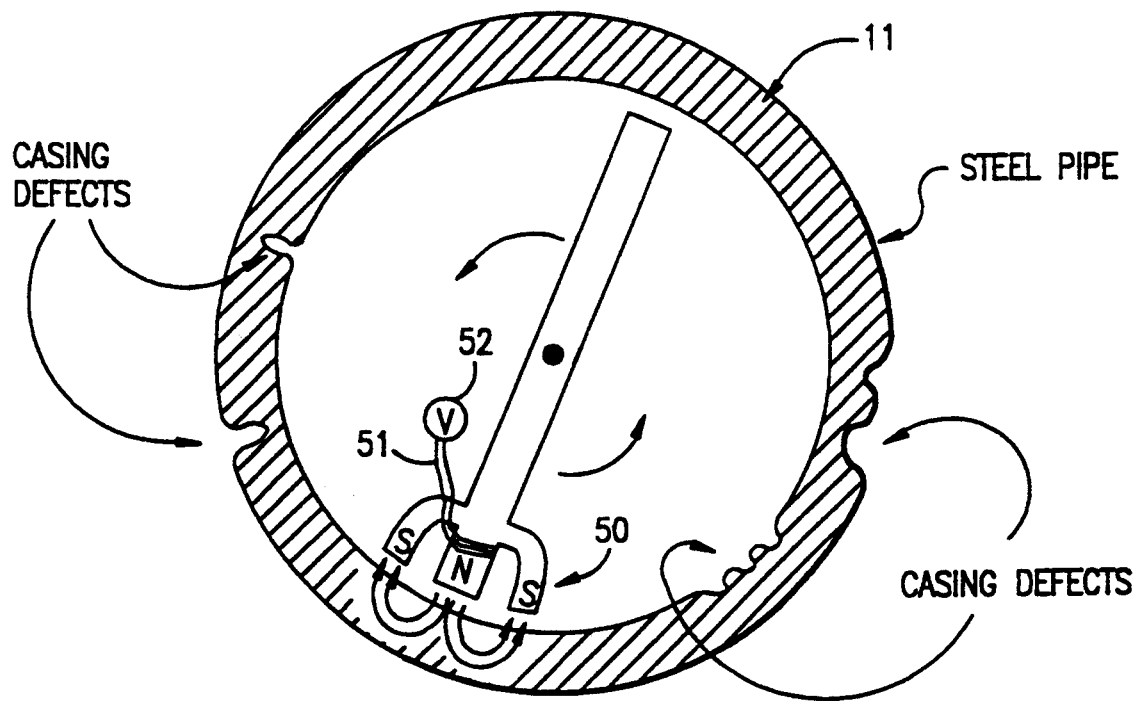
FIG. 1 illustrates a magnetic transducer comprised of a permanent magnet, a coil wound on the pole of the permanent magnet, and a high impedance voltmeter. The transducer is shown on an armature rotating inside a steel casing with various defects both inside and outside the casing. The presence of such defects changes the magnetic flux linkage in the coil during the rotation, thus inducing a voltage which is recorded as a function of angular displacement by the voltmeter.

Referring to FIG. 1, there is illustrated a system for carrying out the 360° azimuthal imaging of casing in accordance with the present invention. This system does not require a liquid medium in the borehole and is not sensitive to density, heterogeneity or production-induced mechanical noise. This system relies on electromagnetically, or magnetically, coupling a transmitter to a receiver through the medium of the magnetically permeable, electrically conductive medium of the ferromagnetic, steel casing. Variations in the degree of coupling can be imaged and interpreted in terms of the amount of conductive material, e.g., steel, in the volume sensed by the measurement. Unlike prior electromagnetically-based casing inspection systems, this system is capable of producing a full 360° azimuthal imaging of the casing.

Figure 2:
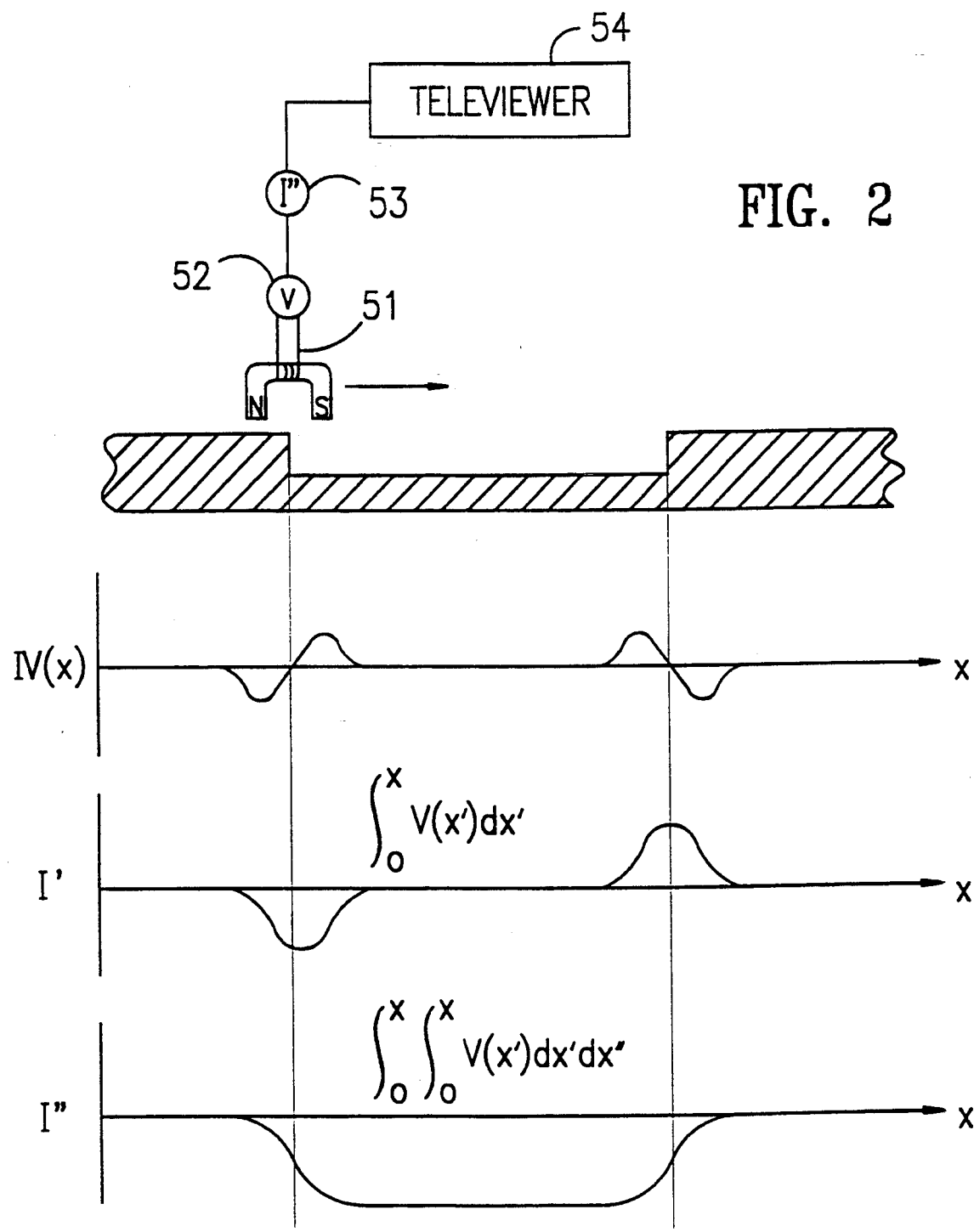
FIG. 2 illustrates the voltage response of a coil wound on a magnet traversing a pit in a magnetic material. The voltage itself produces an anomaly indication which, while it correlates in space with the pit, is a bipolar pulse which returns to zero when the flux is not changing. When twice integrated (I″) with respect to azimuth, the resulting function correlates with the pit morphology.
Figure 3:
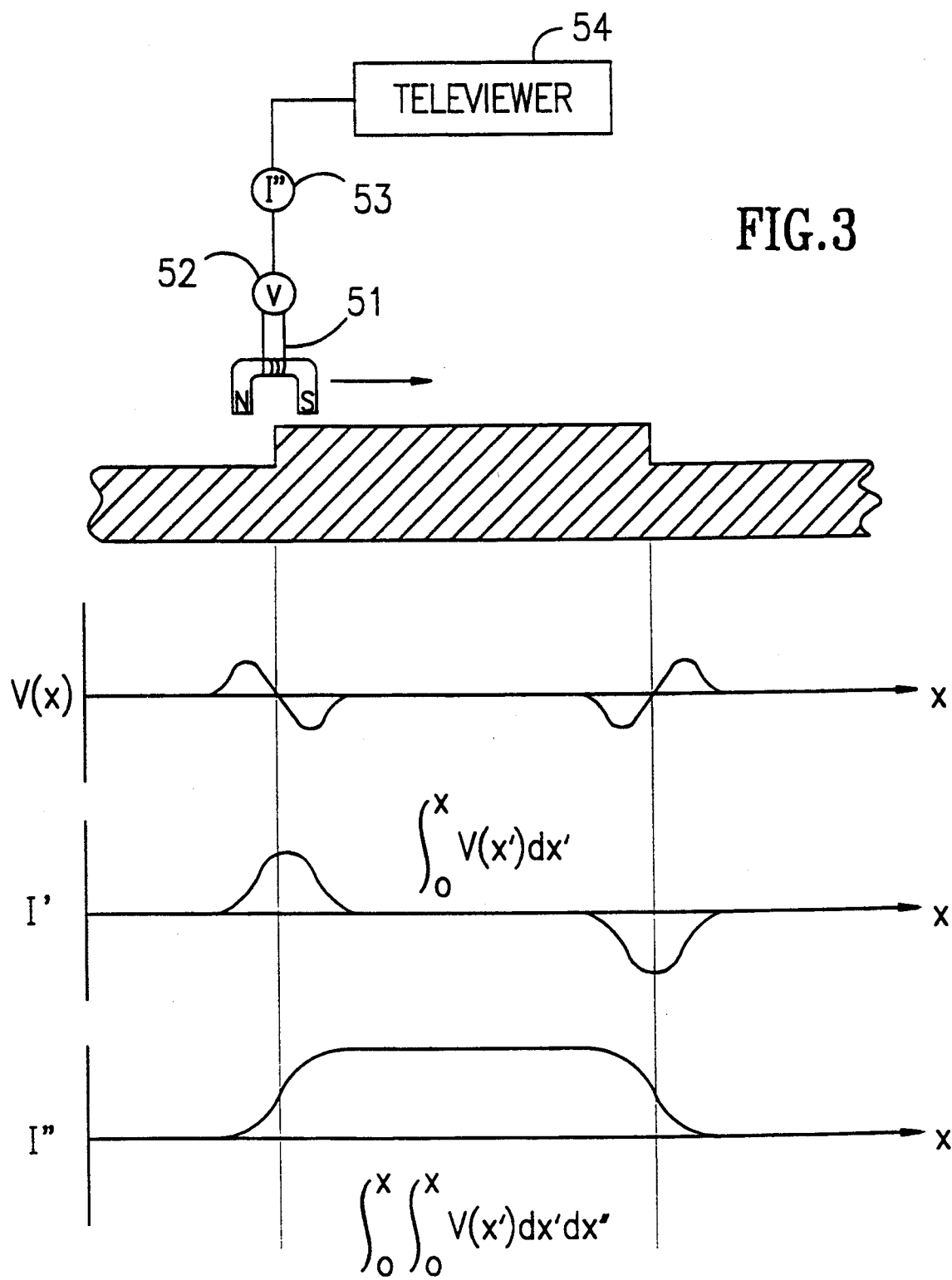
FIG. 3 illustrates that the same signal processing used in FIG. 2 to represent a pit also works when the defect is a raised ledge.

An indication of casing thickness can be obtained using magnetic or electromagnetic principles. One embodiment employing magnetic principles, illustrated in FIG. 1 relies on the coupling, or flux linkage, of a permanent magnet and ferromagnetic steel casing. A permanent magnet 50 is positioned with its poles close to the surface of the steel casing, and is rotated at a constant angular velocity. If the distance between the casing 11 and magnet 50 is constant and the thickness of the casing is also constant, then the flux linkage of the permanent magnet 50 to the casing does not change. A coil 51 wrapped on the magnet will experience no electromotive force. However, if the thickness of the casing varies in the azimuthal direction, the flux linkage will change as the magnet varies in angular position and an electromotive force, or voltage, will arise in the coil. The magnitude of this voltage will be proportional to the change in flux linkage as a function of time, $\Phi/t$, where $\Phi$ is the magnetic flux. For a constant angular velocity this can be correlated linearly with the azimuthal position of the sensor. Thus, transducer voltage records changes in casing thickness. The voltage signal (V) thus generated at 52 is not optimum for interpretation since both thinning and thickening of the ferromagnetic material produce both positive and negative voltages. However, in FIG. 2, the twice integrated signal voltage (I") generated at gives a signal of the same sign for a given type of material defect. As shown in FIG. 2, the coil 51 is wound so that a pit in the casing produces first a negative, then a positive, voltage at the left edge of the pit and the reverse at the right edge of the pit. When this voltage is twice integrated with respect to azimuth, the resulting function correlates with the pit edge locations and depth. Similarly, as shown in FIG. 4, the same data processing will result in a function which correlates with thickening casing. The doubly integrated voltage with respect to azimuth thus provides a function which can be calibrated in terms of the distance from the transducer to the casing. Thus, properly displayed at the televiewer 54, the recorded voltages can be converted into an image of the casing interior. Information is thus obtained from double integrator 53 to construct televiewer-like images of the casing interior surface, exterior surface, and thickness, as described in U.S. Pat. Nos. 3,369,626; 3,718,204; and 3,728,672, and shown at 54 in FIGS. 2 and 3. Information regarding surface texture and thickness and recorded as voltages are encoded in the televiewer image as scan line intensity or color. The images built up from such scans can be made to resemble the pipe as it would appear in ordinary light if brought to the surface; alternatively, false color schemes can be used to enhance the visibility defects of interest.

I claim:

1. A method for 360° azimuthal imaging the thickness of conductive casing in which a transducer is utilized to induce a magnetic flux in the casing and to measure variations in flux density caused by the presence of changes in the thickness of said casing, comprising the steps of:
   a) positioning said transducer inside said casing and in close proximity with the inside wall of said casing,
   b) utilizing said transducer to induce a magnetic flux in said casing along a portion of said casing adjacent said transducer,
   c) rotating said transducer about the axis of said casing to produce a 360° azimuthal scan within said casing,
   d) utilizing said transducer to measure variations in the flux density within said casing during rotation,
   e) continuously repositioning said transducer along a selected length of said casing in juxtaposition with the inside wall of said casing and repeating steps b)–d) at each point,
   f) twice integrating said measured variations in flux density as a function of time,
   g) determining a first change in casing thickness from a consistently positive double integral of said measured flux density variations,
   h) determining a second change in casing thickness from a consistently negative double integral of said measured flux density variations, and
   i) recording the measured variations in flux density for each 360° azimuthal image of the thickness of said casing along said selected length.

2. The method of claim 1 further comprising the steps of:
   a) determining the amount of change in casing thickness in said first direction from a known correlation between casing thickness and positive integral magnitude, and
   b) determining the amount of change in casing thickness in said second direction from a known correlation between casing thickness and negative integral magnitude.

3. A method for electromagnetic imaging of conductive casing comprising the steps of:
   a) rotating an electromagnetic transducer inside conductive casing and continuously advancing said electromagnetic transducer along a length of said casing,
   b) measuring a voltage signal representing variations in flux density within said conductive casing with said electromagnetic transducer as said electromagnetic transducer rotates and advances along said casing,
   c) twice integrating the voltage signal representing said measured variations in flux density as a function of time correlating with casing morphology, a consistently positive double integral of said voltage signal identifying a change in casing thickness in a first direction and a consistently negative double integral of said voltage signal identifying a change in casing thickness in an opposite direction, and
   d) recording said twice integrated voltage signal as a function of azimuthal for each rotational scan versus positioning along the conductive casing to produce an electromagnetic image of casing morphology along said length of conductive casing.

* * * * *

UNITED STATES PATENT AND TRADEMARK OFFICE
CERTIFICATE OF CORRECTION

PATENT NO. : 5,397,985
DATED : March 14, 1995
INVENTOR(S) : W. David Kennedy

It is certified that error appears in the above-indentified patent and that said Letters Patent is hereby corrected as shown below:

In the Title after "Morphology" kindly delete "BY TWICE INTEGRATING MAGNETIC FLUX DENSITY SIGNALS".

Signed and Sealed this

Fourth Day of July, 1995

Attest:

BRUCE LEHMAN

*Attesting Officer*  *Commissioner of Patents and Trademarks*